United States Patent
Shibasaki

(10) Patent No.: US 6,809,059 B2
(45) Date of Patent: Oct. 26, 2004

(54) CATALYST

(75) Inventor: Masakatsu Shibasaki, Tokyo (JP)

(73) Assignee: Johnson Matthey PLC, London (GB)

( * ) Notice: Subject to any disclaimer, the term of this patent is extended or adjusted under 35 U.S.C. 154(b) by 512 days.

(21) Appl. No.: 09/912,319

(22) Filed: Jul. 26, 2001

(65) Prior Publication Data

US 2002/0039961 A1 Apr. 4, 2002

Related U.S. Application Data

(60) Provisional application No. 60/226,578, filed on Aug. 21, 2000.

(51) Int. Cl.[7] .............................. B01J 31/00; C07F 5/00
(52) U.S. Cl. ......................................... 502/171; 534/15
(58) Field of Search .............................. 502/171; 534/15

(56) References Cited

PUBLICATIONS

Martinez et al., Highly Enantioselective Ring Opening of Epoxides Catalyzed by (salen)Cr(III) Complexes, J. Am Chem. Soc. 1995, 117, 5897–5898.

Jacobsen et al., Chapter 38 "Catalyst Immobilization", Comprehensive Asymmetric Catalysis I–III, 1999, 1367–1386.

Tokunaga et al., "Asymmetric Catalysis with Water: Efficient Kinetic Resolution of Terminal Epoxides by Means of Catalytic Hydrolysis", Science, vol. 277, Aug. 15, 1997, pp. 936–938.

Shimizu et al., "A Catalytic Asymmetric Synthesis of Tubifolidine", J. Org. Chem., 1998, 63, pp. 7547–7551.

Matsunaga et al., "Catalytic Enantioselective meso–Epoxide Ring Opening Reaction with Phenolic Oxygen Nucleophile Promoted by Gallium Heterobimetallic Multifunctional Complexes", J. Am. Chem. Soc. 2000, 122, pp. 2252–2260.

*Primary Examiner*—Mark L. Bell
*Assistant Examiner*—J. Pasterczyk
(74) *Attorney, Agent, or Firm*—Mayer Brown Rowe & Maw LLP

(57) ABSTRACT

A catalyst and method for performing a Michael addition reaction between a β-dicarbonyl compound with a cyclic or acyclic enone, where the catalyst comprises a substituted or unsubstituted lanthanum-linked BINOL complex, e.g. a (R,R)-La-linked-BINOL complex (I), are described.

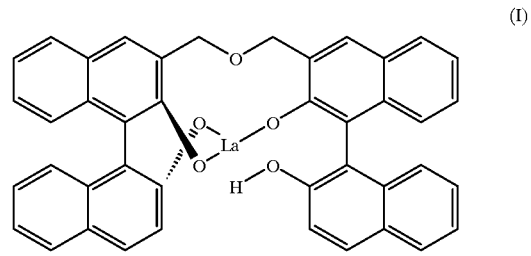

(I)

The catalyst is stable in air, is readily separated from the reaction mixtures and may be reused if desired.

3 Claims, No Drawings

CATALYST

This application claims the benefit of U.S. Provisional Ser. No. 60/226,578, filed Aug. 21, 2000, the entirety of which is incorporated herein by reference.

FIELD OF INVENTION

This invention relates to a compound which is useful as a catalyst for an asymmetric Michael reaction and to a method of preparing a compound by means of a Michael addition reaction.

BACKGROUND OF INVENTION

In recent years, the catalytic asymmetric Michael addition reaction promoted by chiral metal complexes has been recognised as an efficient method for performing enantioselective carbon-carbon bond formation reactions. Herein, a Michael addition reaction is a reaction between an enolate ion, formed from e.g. a ketone or β-dicarbonyl compound and an α, β-unsaturated carbonyl compound, e.g. an enone. Although efficient catalytic asymmetric Michael reactions have been performed, there is still a need for improvements in terms of the range of starting materials with which the catalysts are active and stability of the catalyst. For example, aluminium bis(naphthoxide) may be applied as a catalyst only in reactions employing cyclic enones and is moisture sensitive (see Shibasaki et al, *J. Org. Chem.*, 1998, 63, 7547).

In addition, the development of efficient methods to facilitate the recovery and reuse of asymmetric catalysts remains an important goal in organic chemistry. Intensive efforts have been devoted to develop soluble and insoluble polymer-supported asymmetric catalysts (see for example *Comprehensive Asymmetric Catalysis*; Jacobsen, E. N., Pfaltz, A., Yamamoto, H., Eds., Springer: N.Y. 1999, Chapter 38). However the techniques employed often result in lower enantioselectivities or efficiencies than non-polymer-supported catalysts. Also, because of the difficulties associated with their recovery only a few reusable non-polymer-supported homogeneous asymmetric catalysts suitable for, e.g. Michael reactions, have been developed (for examples see Martinez et al, *J. Am. Chem. Soc.*, 1995, 117, 5897; Tokunga et al, *Science*, 1997, 277, 936). Furthermore, reusable asymmetric Lewis acid catalysts are generally recognised as having a high sensitivity to moisture. Therefore, an increasingly important objective within this area is the development of highly stable asymmetric Lewis acid catalysts that can be recovered and reused.

Recent developments in ligand technology have seen the development of an oxygen-containing linked BINOL, which has the following structure;

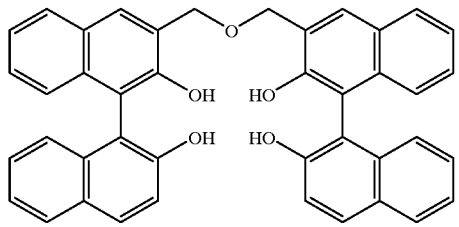

The ligand is chiral and possesses two chiral centres due to the tilting of the naphthoxy moieties relative to each other. The ligand may therefore be described as (R,R), (S,S) or (R,S). The (R,R) form of the linked BINOL has been used to effectively stabilize a Ga—Li complex against ligand exchange with a nucleophile under reaction conditions (see Shibasaki et al, *J. Am. Chem. Soc.*, 2000, 122, 2252) but the group XIII metal complexes such as Al and Ga complexes have poor stability and so there is a desire to provide stable, storable and reusable homogeneous catalyst for the asymmetric Michael addition reaction.

We have found that lanthanum is an efficient Lewis acidic centre for the preparation of a novel, stable, storable and reusable catalyst.

SUMMARY OF THE INVENTION

It is an object of the present invention to provide a catalyst composition comprising a lanthanum-linked BINOL complex selected from the list consisting of;

(i) an unsubstituted lanthanum-linked BINOL complex of general formula (I), and (ii) a substituted lanthanum-linked BINOL complex of general formula (I), wherein at least one of the hydrogen atoms on at least one of the aromatic rings of the complex is substituted with a substituting group.

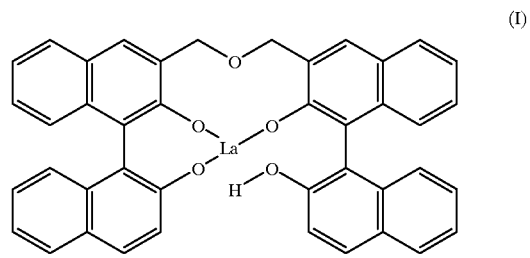

(I)

It is another object of this invention to provide the use of a lanthanum-linked BINOL complex of general formula (I) as a catalyst for a Michael addition reaction.

It is another object of this invention to provide a method of performing a Michael addition reaction comprising reacting a compound that forms an enolate ion and a α, β-unsaturated carbonyl compound in the presence of a catalyst composition comprising a lanthanum-linked BINOL complex of general formula (I).

DESCRIPTION OF THE INVENTION

The powdered La-linked-BINOL complex is readily prepared from La(O$^i$Pr)$_3$ and one equivalent of an oxygen-containing linked-BINOL in a suitable solvent, e.g. THF, followed by removal of solvent under reduced pressure. For example, the La-linked BINOL complex (I) may be prepared from a solution of, e.g. (R,R)-linked-BINOL (II) and a solution of La(O$^i$Pr)$_3$. This is depicted below.

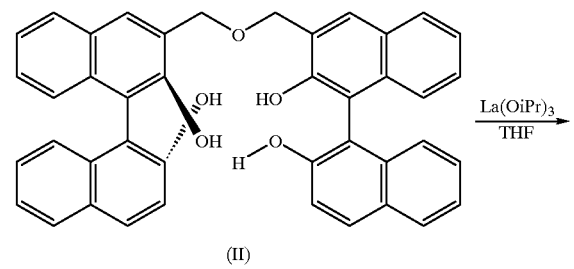

(II)

-continued

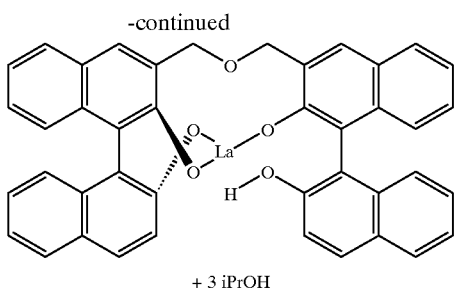

+ 3 iPrOH

It will be appreciated by those skilled in the art that, for example, the solubility of the complex (I) in various solvents may be effected by substituting at least one of the hydrogen atoms on at least one of the aromatic rings with a variety of substituting groups. Such substituting groups include alkyl groups (typically $C_1-C_6$), aryl groups, halide, e.g. chloride groups, nitro groups, amino groups and sulphonyl groups. The substituting groups may be readily introduced during the oxygen-containing linked BINOL ligand synthesis or once the lanthanum has been incorporated to form the complex. It will be appreciated that such substitution is deemed to fall within the scope of the present invention. Preferably the linked BINOL is (R,R)-linked-BINOL (II).

In this complex, it is believed that the lanthanum metal acts as a Lewis acid while the lanthanum naphthoxide moiety acts as a Brønsted base to promote the reaction. The basicity of the naphthoxide moiety may be increased by for example, replacing the proton of the remaining hydroxyl group in (I) with Li, Na or K atoms (see Shibasaki et al, *J. Am. Chem. Soc.*, 2000, 122, 6506).

The powdered La-linked-BINOL complex (I) is highly stable even under air and storable for a long time. This presents a considerable advantage over the previous catalysts.

The complex (I) shows broader substrate generality compared to any reported catalysts in the asymmetric Michael addition reactions. Hence, the complex is effective for the asymmetric Michael addition reaction of a variety of α, β-unsaturated carbonyl compounds such as enones, including both cyclic enones (5 to 9 membered ring), e.g. 2-cyclohexen-1-one or acyclic enones, e.g. methyl-vinyl ketone or 4-phenyl-2-buten-4-one, with compounds that form enolate ions such as β-dicarbonyl compounds, e.g. alkyl malonates such as dibenzyl malonate or 2-ethylacetato-cycloxexanone to afford Michael adducts with good to excellent enantiomeric excesses (ee's).

It will be appreciated by those skilled in the art that the Lewis acidity of the complex (I) lends itself to catalysing other reactions. Other reactions the complex may be suitable as a catalyst for include aldol condensation reactions and a nitro-aldol reactions.

In general the Michael addition reactions may be performed under a range of conditions to suit the various reactants. For example, a catalyst solution may be first prepared in a test tube by dissolving the La-linked-BINOL complex (I) at temperatures in the range −78° C. to room temperature (ca 20° C.) in a suitable solvent such as 1,2-dimethoxyethane (DME) and/or tetrahydrofuran (THF) and stirring the mixture for 5 min at the same temperature. To this may then be added the α, β-unsaturated carbonyl compound such as an enone, e.g. 2-cyclohexen-1-one and the enolate ion forming compound such as a β-dicarbonyl compound, e.g. dibenzyl malonate. The mixture can then be stirred for 5 min. then the reaction mixture allowed to slowly warm if necessary to room temperature (ca 20° C.). After a period of time, e.g. about 24 to 120 hours hours, the product can be isolated. Various techniques for product isolation and purification are known to those skilled in the art and may be used in the present invention. For example, the mixture may be diluted with a suitable solvent e.g. with ethyl acetate, washed with saturated aqueous $NH_4Cl$ brine, and then dried over $MgSO_4$. The solvent can then be evaporated under reduced pressure and the residue was purified, e.g. by flash column chromatography ($SiO_2$, hexane/acetone 10/1) to give the final product typically in yield >60% and in many cases >90% and with enantiomeric excess (ee) typically >70% and in many cases >99%.

The non-polymer-supported homogeneous asymmetric La-linked BINOL complex (I) may be recovered from the reaction mixture and reused. Typically, the complex may be isolated by precipitation from the reaction solution. For example, the complex may be precipitated in the reaction vessel by addition of a suitable solvent such as a hydrocarbon, e.g. pentane or hexane to the DME or THF reaction mixture, due to the large difference of solubility between the complex and product. After removal of the product-containing supernatant solution, by e.g. filtration or decantation, followed by drying, e.g. under reduced pressure, the La-linked-BINOL complex (I) may be recovered as a powder and reused.

A wide range of products may be prepared according to the method of the present invention. The range of compounds includes but shall not be limited by the following;

(R)-3-[bis(Benzyloxycarbonyl)methyl]cyclohexanone,
(R)-3-[(bis(Bentyloxycarbonyl)methyl]cyclopentanone,
(R)-3-[bis(Methoxycarbonyl)methyl]cyclopentanone,
(R)-3-[bis(Methoxycarbonyl)methyl]cyclohexanone,
(R)-3-[bis(Benzyloxycarbonyl)ethyl]cyclohexanone,
(R)-3-[bis(Benzyloxycarbonyl)methyl]cycloheptanone,
(R)-3-[bis(Methoxycarbonyl)methyl]cycloheptanone,
(R)-3-[bis(Methoxycarbonyl)methyl]cyclooctanone,
(R)-3-[bis(Benzyloxycarbonyl)methyl]cyclononanone,
(R)-Benzyl 2-(bentyloxycarbonyl)-3-methyl-5-oxo-5-phenylpentanoate,
(R)-Methyl 2-(methoxycarbonyl)-3-methyl-5-oxo-5-phenylpentanoate, and
(S)-Ethyl 2-oxo-1-(3-oxobutyl)-cyclohexanecarboxylate.

The following examples are intended to illustrate more fully specific embodiments of the present invention without acting as a limitation on its scope.

The enantiomeric excesses (ee's) of the products were determined by HPLC analysis. HPLC was performed on JASCO HPLC systems consisting of the following: pump, 880-PU or PU-980; detector, 875-UV or UV-970, measured at 254 nm: column, DAICEL CHIRALPAK AS, AD, DAICELCHIRALCEL OD or OJ; mobile phase, hexane-2-propanol; flow rate, 0.30–1.0 ml/min. Reactions were carried out in dry solvents under an argon atmosphere, unless otherwise stated. Tetrahydrofuran (THF) and dimethoxyethane (DME) were distilled from sodium benzophenone ketyl. Toluene and pentane were distilled from sodium. $La(O^iPr)_3$ was purchased from Kojundo Chemical Laboratory Co., LTD. Other reagents were purified by the usual methods.

EXAMPLE 1

This example demonstrates a procedure for the preparation of a (R,R)-La-linked-BINOL complex. To a stirred solution of (R,R)-linked-BINOL (II) (1.01 g, including 7.4 w/w % solvent (diethyl ether and hexane), 1.5 mmol), in THF (10 mL) at −78° C. was added a solution of La(OiPr)$_3$ (7.5 mL, 1.5 mmol, 0.2 M in THF, freshly prepared from the powder of La(OiPr)$_3$ and dry THF). The solution was stirred for 5 h at room temperature, and then the solvent was evaporated under reduced pressure. The resulting residue was dried for 2 h under reduced pressure (ca. 4 mmHg) to afford pale yellow powdered (R,R)-La-linked BINOL complex (1.13 g. 1.5 mmol). This powdered catalyst can be stored for at least 4 weeks under air at room temperature. For example no change in catalytic activity, in terms of both chemical yield and enantiomeric excess (ee), was observed in a standard reaction between 2-cyclohexen-1-one and dibenzyl malonate using the same sample of La-linked-BINOL complex (at 10 mol % in DME for 72 hours at room temperature) even after 4 weeks storage under air (95% yield. >99% ee).

EXAMPLE 2

This example demonstrates a procedure for performing a catalytic asymmetric Michael addition reaction promoted by the (R,R)-La-linked-BINOL complex. To (R,R)-La-linked-BINOL complex (45.1 mg, 0.06 mmol) in a test tube at −78° C. was added DME (1.5 mL), and the mixture stirred for 5 min at the same temperature. Then, 2-cyclohexen-1-one (1) (58 μL, 0.60 mmol), and dibenzyl malonate (2) (150 μL, 0.60 mmol) were added. The mixture was stirred at −75° C. for 5 min. then the cooling bath (dry-ice/acetone) removed and the reaction mixture was allowed to warm to 4° C. After 85 h, the mixture was diluted with ethyl acetate, washed with sat. aq. NH$_4$Cl brine, and then dried over MgSO$_4$. The solvent was evaporated under reduced pressure and the (R)-3-[bis(Benzyloxycarbonyl) methyl] cyclohexanone product (3) purified by flash column chromatography (SiO$_2$, hexane/acetone 10/1) to give 3 (223.8 mg, 0.588 mmol, yield 98%) in >99% ee.

This reaction and further reactions are depicted by the following reaction schemes;

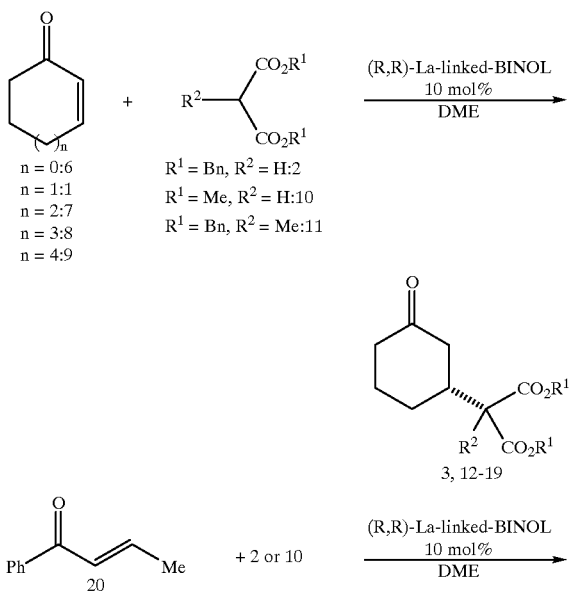

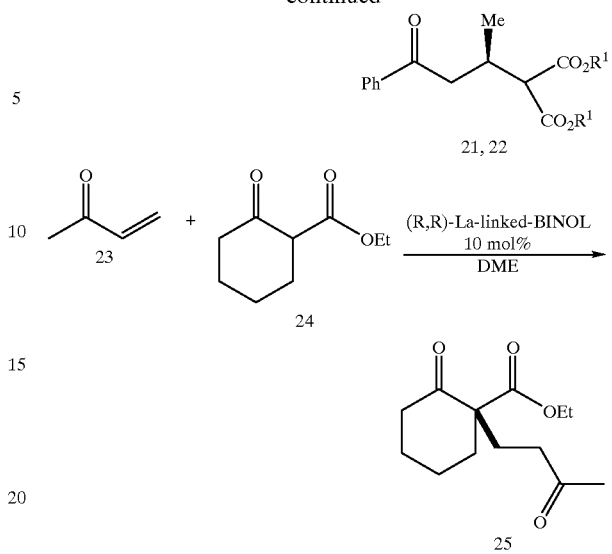

where, Bn=Benzyl, (C$_6$H$_5$CH$_2$); Me=Methyl (CH$_3$); Ph=Phenyl (C$_6$H$_5$); and Et=Ethyl (C$_2$H$_5$).

The Michael products 3, 12, 13, 16, 17 and 19 were synthesized following the general procedure. Further modifications to the method were practised as follows; Michael reaction was performed at room temperature for compound 14, 15 and 18, at −40° C. for compound 21 and 22 and at −30° C. for compound 25. A DME/THF=9/11 co-solvent system was used for 15 and 18. 24 was added dropwise over 24 h in the synthesis of 25.

A summary of the results may be found in Table 2.

TABLE 2

| Experiment | Enone | β-dicarbonyl compound | Temp (° C.)[a] | Time (hours) | Product | Yield[b] (%) | ee[c] (%) |
|---|---|---|---|---|---|---|---|
| 1 | 6 | 2 | 4 | 85 | 12 | 85 | >99 |
| 2 | 6 | 10 | 4 | 85 | 13 | 96 | >99 |
| 3 | 1 | 2 | Rt (ca 20° C.) | 72 | 3 | 94 | >99 |
| 4 | 1 | 2 | 4 | 85 | 3 | 98 | >99 |
| 5 | 1 | 10 | Rt (ca 20° C.) | 72 | 14 | 95 | >99 |
| 6[d] | 1 | 11 | Rt (ca 20° C.) | 84 | 15 | 84 | 98 |
| 7 | 7 | 2 | 4 | 85 | 16 | 96 | >99 |
| 8 | 7 | 10 | 4 | 85 | 17 | 97 | >99 |
| 9[d] | 8 | 10 | Rt (ca 20° C.) | 96 | 18 | 82 | 99 |
| 10 | 9 | 2 | 4 | 120 | 19 | 61 | 82 |
| 11 | 20 | 2 | −40 | 56 | 21 | 97 | 78 |
| 12 | 20 | 10 | −40 | 56 | 22 | 95 | 74 |
| 13[e] | 23 | 24 | −30 | 36 | 25 | 97 | 75 |

[a]Rt = Room temperature.
[b]Isolated yield.
[c]Determined by HPLC analysis.
[d]The reaction was carried out in DME/THF (9:1).
[e]24 was added drop-wise over 24 hours.

These results demonstrate the high activity across a range on enone substrates achieved by the present invention.

EXAMPLE 3

This example demonstrates a method for recycling the La-linked-BINOL complex. To (R,R)-La-linked-BINOL complex (225 mg, 0.3 mmol 10 mol %) was added DME (7.5 mL) at −78° C. then the mixture was warmed gradually until the complex was dissolved completely. To the DME solution of the complex were added 2-cyclohexen-1-one (1) (0.29 mL, 3.0 mmol) and dibenzyl malonate (2) (0.75 mL, 3.0 mmol) at −78° C. The reaction mixture was warmed to 4° C. and stirred for 110 h at the same temperature to complete the reaction. After completion of the reaction, pentane (30 mL) was added to the reaction mixture at 0° C., which was allowed to stand for 1 h at the same temperature. The supernatant liquid was separated via cannula, and the residual precipitates were washed with pentane (10 mL×2). The combined supernatant liquid was quenched by addition of 1N aqueous HCl solution, extracted with $Et_2O$, dried over $Na_2SO_4$, filtered, and concentrated. The resulting residue was purified by flash column chromatography (silica gel, 20% acetone in hexane) to yield 3 (940.3 mg, 82%) as a colorless oil. The precipitate was dried under reduced pressure for 30 min to yield the (R,R)-La-linked-BINOL complex as a pale-yellow powder, which was treated with THF (6.0 mL) at 0° C. for 4 h prior to recycle. After removal of THF under reduced pressure for 1 h, the recovered complex was reused.

The recovered complex at 10 mole %, promoted the Michael reaction described above (in DME for 110 hours at 4° C.) between 2-cyclohexen-1-one and dibenzyl malonate to afford the desired Michael adduct with very high ee, i.e. 98% ee, even after fourth use.

Thus there has been shown and described a catalyst and method for performing Michael addition reactions which fulfil all the advantages sought. It will be apparent to those skilled in the art, however, that many changes, variations, modifications and other uses and applications for the subject catalyst and method are possible, and also such changes, variations, modifications, and other uses and applications which do not depart from the spirit and scope of the invention are deemed to be covered by the invention which is limited only by the claims which follow.

What is claimed is:

1. A catalyst composition comprising a BINOL-lanthanum complex selected from the group consisting of;
   (i) an unsubstituted BINOL-lanthanum complex of general formula (I), and
   (ii) a substituted BINOL-lanthanum complex of general formula (I), wherein at least one of the hydrogen atoms on at least one of the aromatic rings of the complex is substituted with a substituting group.

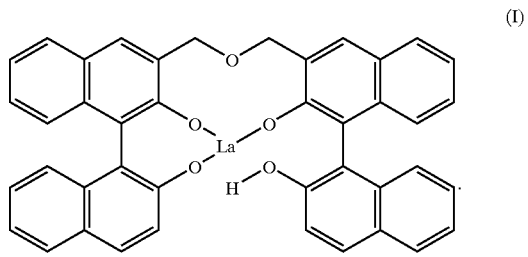

(I)

2. A catalyst according to claim 1 wherein the BINOL-lanthanum complex is unsubstituted (R,R) BINOL-lanthanum.

3. A catalyst according to claim 1 wherein the substituting group is an alkyl group, an aryl group, a halide, a nitro group, an amino group, or a sulphonyl group.

* * * * *